(12) United States Patent
Assmann et al.

(10) Patent No.: US 8,447,381 B2
(45) Date of Patent: May 21, 2013

(54) METHOD AND APPARATUS FOR CONTROLLING A CONTRAST AGENT INJECTION FOR MAGNETIC RESONANCE IMAGING

(75) Inventors: Stefan Assmann, Erlangen (DE); Andrea Hopf, Gaal (AT); Christof Krellmann, Erlangen (DE); Michaela Schmidt, Uttenreuth (DE); Peter Schmitt, Weisendorf (DE); Michael Zenge, Nuernberg (DE)

(73) Assignee: Siemens Aktiengesellschaft, Munich (DE)

( * ) Notice: Subject to any disclaimer, the term of this patent is extended or adjusted under 35 U.S.C. 154(b) by 254 days.

(21) Appl. No.: 12/698,276

(22) Filed: Feb. 2, 2010

(65) Prior Publication Data
US 2010/0198055 A1    Aug. 5, 2010

(30) Foreign Application Priority Data
Feb. 2, 2009    (DE) .......................... 10 2009 007 047

(51) Int. Cl.
*A61B 5/055*    (2006.01)

(52) U.S. Cl.
USPC .......................................................... 600/420

(58) Field of Classification Search
USPC ............. 600/407, 410, 420, 431, 432; 702/19
See application file for complete search history.

(56) References Cited

U.S. PATENT DOCUMENTS

| | | | |
|---|---|---|---|
| 7,413,123 B2* | 8/2008 | Ortenzi ......................... 235/385 |
| 2007/0083152 A1* | 4/2007 | Williams et al. ................. 604/65 |
| 2007/0225601 A1* | 9/2007 | Uber et al. ..................... 600/431 |
| 2008/0119715 A1* | 5/2008 | Gonzalez Molezzi et al. ............................ 600/407 |
| 2008/0310581 A1 | 12/2008 | Feuerlein et al. |
| 2009/0214094 A1* | 8/2009 | Williams et al. .............. 382/131 |
| 2010/0113887 A1* | 5/2010 | Kalafut et al. ................ 600/300 |

* cited by examiner

*Primary Examiner* — Ruth S Smith
(74) *Attorney, Agent, or Firm* — Schiff Hardin LLP

(57) ABSTRACT

In a method and magnetic resonance system for controlling a contrast agent injector used with a magnetic resonance imaging scanner of the system, a user interface is displayed at the control panel of the scanner, for configuring the operating parameters of the injector connected to the magnetic resonance imaging scanner and for controlling the injector in accordance with the operating parameters configured on said user interface, from the scanner control panel.

11 Claims, 2 Drawing Sheets

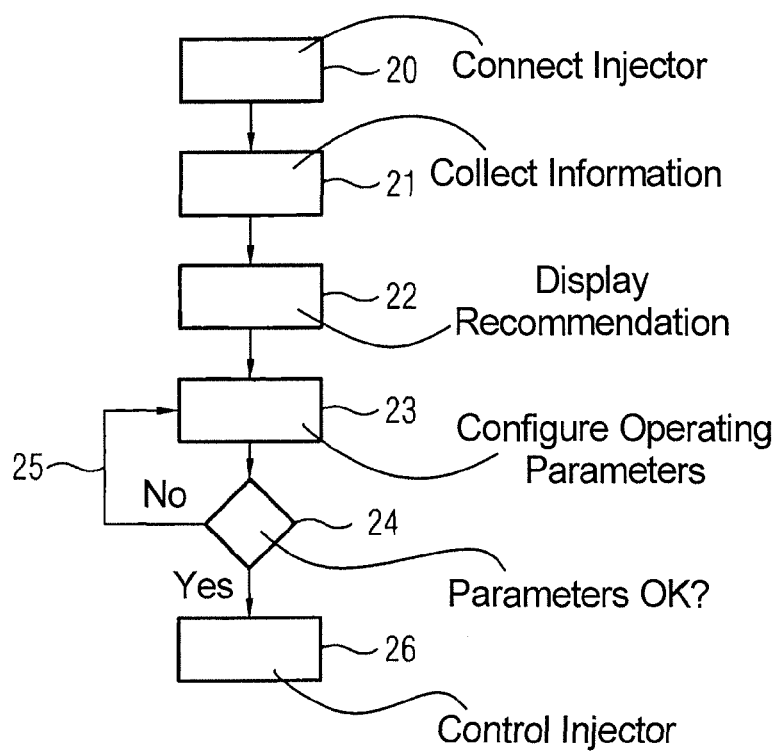

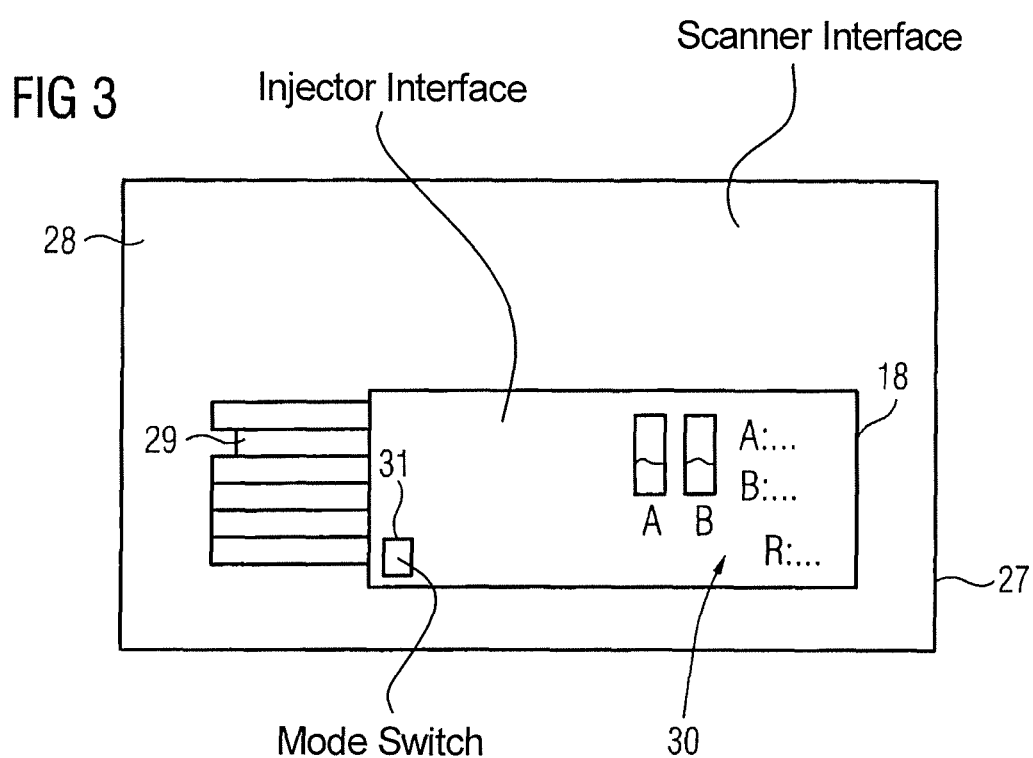

METHOD AND APPARATUS FOR CONTROLLING A CONTRAST AGENT INJECTION FOR MAGNETIC RESONANCE IMAGING

BACKGROUND OF THE INVENTION

1. Field of the Invention

The present invention relates to a process for controlling a contrast agent injector for a magnetic resonance imaging scanner as well as a magnetic resonance imaging scanner.

2. Description of the Prior Art

Many imaging processes used in magnetic resonance imaging, such as in functional magnetic resonance imaging, require injections of various contrast agents in the patient either during or shortly prior to the data acquisition procedure. In order to inject this contrast agent, a peripheral unit (injection device) is used and it is conventional to configure an injection formula in the form of operating parameters for this device, composed basically of the injection dosage and injection rate. This takes place on a small monitor attached to the injector. This means that in order to control the injector, an operator must enter the configuration directly into the injector, for example through a user interface, then confirm the configuration, so that the activated injector is subsequently controlled in accordance with the appropriately configured operating parameters.

This, however, requires that the operator constantly change has her view (gaze) between the control panel of the magnetic resonance imaging scanner, such as a console, and the injector itself, which requires substantial effort.

SUMMARY OF THE INVENTION

An object of the invention is to provide a process for controlling a contrast agent injector, which by comparison is an improvement.

In order to accomplish this task for a process as described above, in accordance with the invention a user interface for configuring the operating parameters of the injector used with the magnetic resonance imaging scanner is displayed on the control panel of the magnetic resonance imaging scanner such that the injector may be controlled according to the operating parameters that have been entered through the user interface.

There are newer injector models available that include an interface used for various purposes, in particular a CAN-interface (CAN open is common), allowing the injector to be connected through a bus system to other devices. In accordance with the present invention, an injector is first connected to the magnetic resonance imaging scanner with an appropriate connector such that there exists a communication pathway between the magnetic resonance imaging scanner and the injector. Furthermore, the scanner control console of the magnetic resonance imaging scanner is configured with a user interface for entering the operating parameters for the injector, which provides a number of benefits. With such a coupling of the injector and the magnetic resonance imaging scanner, the injector configuration can be controlled and modified at the magnetic resonance imaging scanner, so that the user need not alternate between the control panel of the magnetic resonance imaging scanner and the injector, but instead is able to comfortably operate both systems from the control panel of the magnetic resonance imaging scanner. Furthermore, there is the advantage that the magnetic resonance imaging scanner has access to additional patient specific and/or examination specific data, for example through various information systems or from data entered by the operator, which may be of great benefit in the configuration of the injector. Overall, the present invention offers comfortable operation, and allows for access by the operator to a larger array of data, thereby helping to limit the chance of input error.

A CAN-bus may be used for communication between the magnetic resonance imaging scanner, particularly the control panel, and the injector. CAN-bus systems, particularly the CAN open protocol, are widely used in the field of medical technology as well, and as a result, such a bus system with an existing appropriate interface on the magnetic resonance imaging scanner/control panel and the injector can be used advantageously for communication.

The user interface may contain input fields for an injection formula, including at least the injection dosage and the injection rate. With a user interface of this type, it is possible for the operator to make configurations in a particularly simple manner, as he or she is already familiar with this type of user interface for injectors. The injection dosage and the injection rate are the most important operating parameters of the injector relevant to magnetic resonance imaging.

A particular benefit is that the same user interface that would be displayed at the injector, which is usually proprietary to the manufacturer of the user interface of the injector. Thus, there is no need for the operator to become familiar with a new user interface, since the operator is essentially using the same user interface as was used in the direct operation of the injector—which, it is understood, can, and should still be possible. To allow this, it is not necessary that the user interface displayed at the control console of the scanner be identical to the injector interface, but rather, it is sufficient for the proprietary "look and feel" of the injector interface be conveyed. In order to accomplish this, basically two possibilities are conceivable.

In a first variation of the present invention, when an injector is connected, the injector type is recognized and/or entered, at which point a specific user interface for that injector type is displayed. For this purpose, user interfaces or input templates of various manufacturers and various models are stored, for example, in a data base in the magnetic resonance imaging scanner or the control panel. When an injector is connected to the magnetic resonance imaging scanner, then it is possible for either the user to select the correct injector type from a list, or for an automatic recognition to take place. Possibilities using various bus systems, particularly also the CAN-bus, or communication connections for identification of a connected device or device type, are known and can be applied beneficially in the following process.

In a second variation, the user interface that is displayed on the injector can be transferred and displayed on the magnetic resonance imaging scanner. In this case, a type of remote control is obtained, as is known in the use of computers (similar to a remote desktop connection). The user interface to be displayed of the injector display screen is transferred to the control panel of the magnetic resonance imaging scanner, and displayed there as well. Furthermore, the input and manipulation possibilities are taken over—which means that the operator can work at the control panel in exactly the same manner as he or she would if he were working directly on the injector.

It should be noted that, at least with the first variation, it is also possible to control the injector directly through the control panel. Otherwise, the operating parameters can be transferred to the injector, which then accordingly controls itself.

In a preferred design of the method in accordance with the invention, the configured operation parameters can be assessed through the user interface, particularly an injection formula, based on accessed patient specific information regarding patient tolerance taken from an information system, particularly from hospital records and/or radiology records and/or electronically stored patient files. In other words, further sources of information are used advantageously to aid the operator in configuring the injector, and to protect the patient. For example, if it is known from radiology records, hospital records, or electronic patient files that the patient suffers renal insufficiency, then the contrast agent dosage can be assessed (set) accordingly. Furthermore, an assessment can take place based on other characteristics of the patient, such as height, weight or sex. In this manner it is possible for the control panel to display a warning in the case of a negative assessment and/or an automatic adjustment can be made to the entered operating parameters so as to comport the operating parameters with the patient's tolerance. The operator is thereby informed that the entered configuration of the injector has been determined to be not compatible with the patient. Furthermore, if an automatic adjustment is to be carried out, this can be presented to the operator as a recommendation. If, for example, the patient suffers renal insufficiency, then the operator is able to reduce the contrast agent dosage accordingly, or elect to use an alternative process that does not require the use of a contrast agent. In this manner, supplementary information is used advantageously in order to ensure patient tolerance, and to aid the operator in making an entry. In this manner, improved control of the injector is made possible.

In a further embodiment of the present invention, the user interface can display a recommendation, particularly from a data base, for the operating parameters based on accessed patient specific information, particularly the age and/or height and/or weight and/or information pertaining to renal function, from an information system, specifically hospital records and/or radiology records and/or electronic patient files. In this design, a recommendation from the magnetic resonance imaging scanner, specifically the control panel itself, is selected from a data base based on the patient specific and/or examination specific information, which is tailored specifically to the patient. The data base does not need to be stored in the magnetic resonance imaging scanner for this purpose, but may instead, for example, be a part of the radiology records. This recommendation is then simultaneously displayed to the user on the user interface, so that in the simplest case, the user need merely confirm agreement with the recommendation, so a particularly simple control of the injector is obtained. It is understood that patient-specific and/or examination-specific information that is entered manually in the magnetic resonance imaging scanner may be used. As an alternative to the use of a data base with recommendations for certain values of the patient specific and/or examination specific information, it is also possible to calculate the contrast agent dosage on the magnetic resonance imaging scanner, specifically on the control panel. This task is carried out for the user, making the operation simpler, and thereby generally avoiding the risk of input error.

Many injectors have different modes of operation, which are for the safety of the patient as well as for operational safety. In this context, a standby mode, wherein an injection of a contrast agent is possible, and a safe mode, wherein an injection of a contrast agent is not possible, may be used in such an injector. With an injector of this type, it must first be set in the standby mode before the data is actually entered, in other words, it must be "active." It is then possible to switch back and forth between the standby mode and the safe mode through another user interface in the control panel. This control possibility can also be realized through the control panel of the magnetic resonance imaging scanner. A particular benefit can also be obtained by conveying a modus state to the magnetic resonance imaging scanner in which, with a user initiated start, imaging with the magnetic resonance imaging scanner in the safe mode will display a warning and/or a starting of the imaging will be terminated when in the safe mode. If the injector is not "active," then no useful magnetic resonance imaging can be carried out, in order that the operator may be warned and/or an imaging is prevented entirely. In this manner, the communication connection between the injector and the magnetic resonance imaging scanner is used advantageously. If it is furthermore possible to switch to the standby mode on the injector as well, then it is also possible to send a message to the control panel when switching to standby mode. In this manner, the operator at the magnetic resonance imaging scanner is informed that it is possible to begin an imaging.

Aside from the method, the present invention also encompasses a magnetic resonance imaging scanner, having a control panel with an input device and a display as well as a port designed for connecting an injector, wherein the control panel is designed to display a user interface for configuring operating parameters of an injector connected to the magnetic resonance imaging scanner. In particular, a magnetic resonance imaging scanner of this sort can be designed such that it can execute the method in accordance with the invention. A magnetic resonance imaging scanner of this type offers not only the possibility for connecting an injector to the scanner, but also for operating the injector through the control panel of the magnetic resonance imaging scanner itself. In this manner, an operator conducting a magnetic resonance imaging with a contrast agent no longer needs to switch between the control panel of the magnetic resonance imaging scanner and the injector, but rather is able to operate both systems simultaneously. In addition, it is also understood that with the magnetic resonance imaging scanner in accordance with the invention there is also the advantage of having the possibility to access various information systems or manually entered data on the magnetic resonance imaging scanner itself, as has already been explained in detail in the description of the process.

BRIEF DESCRIPTION OF THE DRAWINGS

FIG. 1 schematically illustrates a magnetic resonance imaging scanner in accordance with the invention.

FIG. 2 is a flowchart of an embodiment in accordance with the invention.

FIG. 3 shows an example of a display at a user interface on the control panel of the magnetic resonance imaging scanner in accordance with the invention.

DESCRIPTION OF THE PREFERRED EMBODIMENTS

FIG. 1 shows a magnetic resonance imaging system 1 in accordance with the invention. It includes, as is customary, a scanner (data acquisition unit) 2 with a scanner table 3, as is generally known and need not be explained further herein. The magnetic resonance imaging system 1 furthermore includes a control panel 4 shown in the example as a console 5 composed of a display 6 and an input device 7. Configuration of the magnetic resonance imaging system 1 may be carried out for an imminent imaging through the control panel 4. The magnetic resonance imaging system 1 is in constant communication with an information system 9, i.e. a radiology records system or a hospital records system in which, in the present example, electronic patient files 10 are also stored. In addition, the information system 9 also contains a data base 11, which lists potential configurations of an injector dependant on certain patient specific and examination specific information, which will be explained in greater detail in the following. The data base 11 may also be stored in the magnetic resonance imaging system 1 itself.

Furthermore, the magnetic resonance imaging system 1 includes a port 12, preferably a CAN interface, allowing an injector 13 for contrast agents having an appropriate CAN interface 14 to be connected, so that there is a communication pathway 15 between the magnetic resonance imaging system 1 and the injector 13. The injector 13, which is of a specific type, i.e. manufacturer and model, also has a display 32 and an input device 16, through which the operating parameters for controlling the injector 13 can be entered. The injector 13 also has a standby mode, wherein the injection of a contrast agent is possible, and a safe mode, whereby the injection of a contrast agent is not possible. A switch 17 allows for switching between the two modes, i.e., the injector may be switched to "active."

The magnetic resonance imaging system 1 is furthermore designed such that it displays a user interface 18 on the display 6 of the control panel 4 for the connected injector 13, so the operating parameters for the injector 13 may be configured and the injector can be controlled, from the control panel 4. It is thus possible to configure the operating parameters of the injector 13 for an upcoming injection formula, including at least the injection dosage and the injection rate, from the control panel 4 of the magnetic resonance imaging system 1, which can then be transmitted via the communication pathway 15 (i.e. the CAN bus) to the injector 13, which is in turn controlled accordingly.

The user interface 18 can basically conform to a proprietary user interface of the injector 13. For this, the control panel 4 is designed in a first version to recognize the injector type when the injector 13 is connected. At this point, an injector-specific user interface can be displayed from the data base 19 associated with the control panel 4, which has the "look and feel" of the injector 13. It is understood that a user selection of the injector type is also possible as an alternative to the automatic recognition of the injector 13.

In a second version, the control panel is designed such that the user interface 18 of the display 32 for the injector 13 which is to be displayed can be called and displayed through a remote connection. In this case the same configuration possibilities exist as on the injector 13 itself. The control panel 4 in this case takes on the display that is intended for the injector 13.

It should be noted that with both versions, the user interface 18 can either occupy the entire surface of the display 6, or only a part of the display 6. In the second case, the user interface 18 is integrated in the operating concept of the magnetic resonance imaging system 1.

It should also be noted that the control panel 4 is also designed so that it is possible to switch between the standby mode and the safe mode either through said, or through an additional user interface 18. This operating possibility for the injector 13 is also available on the control panel 4 of the magnetic resonance imaging scanner. In any case, a modus signal is transmitted through the communication pathway 15 to the magnetic resonance imaging system 1, in order that with a user-initiated start, an imaging with the magnetic resonance imaging system 1 can be checked to see if the standby mode or the safe mode is currently active. If the safe mode is currently active, then a warning signal will be displayed, and the imaging process will be unable to start. To execute a magnetic resonance imaging, which requires a contrast agent, is of no practical value without the possibility of injecting the contrast agent.

The design of the magnetic resonance imaging system 1 also takes into account that with a switching to the standby mode or to the safe mode at the injector 13 itself, i.e. with the switch 17, an appropriate signal is sent to the control panel 4; for example, in a pop up window on the display 6.

FIG. 2 shows a flow chart of the basic steps of the method in accordance with the invention. In step 20, the injector 13 is first connected to the magnetic resonance imaging system 1 and from said automatically recognized. A user interface 18 is selected which is specific to the injector type, and is integrated to the operating concept of the display 6 on the magnetic resonance imaging system 1. In step 21, the patient-specific and examination-specific information is collected through communication with the information system 9, particularly the electronic patient files 10, but also information directly entered in the console 5. This information, primarily the age, height, weight and renal function of the patient, and also the region to be examined, is used by the control panel 4 in order to make a recommendation for the operating parameters of the injector 13. This can be supplemented by the data base 11, and it is also possible to override this recommendation by calculating the injection dosage and injection rate as well as other operating parameters and entering this into the control panel 4 manually.

This recommendation is then displayed in step 22 together with the user interface 18 on the display 6 of the control panel 4.

It is should be noted that step 21 is optional, and it may be sufficient in step 23 to use the operating parameters configured by the user according to the evaluation concept explained in the following.

In step 23, then, the configuration of the operating parameters for the injector 13 entered by the user are carried out. This can take place when the recommendation submitted in step 21 is simply confirmed, or it is also possible to make modifications or to enter entirely new operating parameters.

In step 24, which is also optional, an evaluation of the operating parameter configuration is executed in the control panel with regard to patient specific information. As an example, a possible patient renal insufficiency is of particular note, if the contrast agent dosage entered is too high. In this case, it shall be determined that this exceeds the patient's tolerance level. If such is the case, then a pop up window will display this information, and a recommendation will be made, suggesting for example a lower dosage of contrast agent, or the execution of a magnetic resonance imaging without a contrast agent. In the case of a negative evaluation of the patient tolerance, as is indicated by the arrow 25, it is possible for the user to go back and modify the configuration in step 23.

If it is determined that the operating parameters are within the patient's tolerance level, or if the user insists on a configuration that exceeds the patient's tolerance, then in step 26 the injector 13 may be controlled according to the configuration of the operating parameters.

FIG. 3 shows a possible display 27 on the display 6, which contains the user interface 18. The user interface 18 can be seen to be integrated in a user interface 28 of the magnetic resonance imaging scanner 2, and can be selected via a control panel 29 during several steps of the examination plan. Input fields 30 for an injection formula are shown in the user interface 18, whereby the contrast agent dosage is indicated as "A", the saline solution dosage as "B", and the rate is indicated as "R". A further control element 31 offers the possibility to switch between the standby mode and the safe mode.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a contrast agent injector in a magnetic resonance imaging apparatus, comprising the steps of:
    providing a communication path between a contrast agent injector, connected to a magnetic resonance scanner, and a control panel of the magnetic resonance imaging scanner;
    displaying a user interface for said contrast agent injector at said control panel of said magnetic resonance scanner;
    via said user interface, configuring operating parameters for said contrast agent injector to produce preliminary operating parameters for said contrast agent injector;
    storing information in a database that is relevant to treatment of a specific patient with contrast agent;
    from said user interface, accessing said information from said database and displaying said information at said user interface at said control panel;
    in a processor connected to said control panel, automatically evaluating, dependent on said information, said preliminary operating parameters for said contrast agent injector;
    when evaluation in said processor of said operating parameters dependent on said information indicates the preliminary operating parameters are not appropriate for said specific patient, automatically generating, from said processor, a warning at said user interface and, in said processor, automatically generating final operating parameters for said contrast agent injector from said preliminary operating parameters; and
    controlling operation of said contrast agent injector according to said final operating parameters.

2. A method as claimed in claim 1 comprising employing a CAN-bus as said communication path.

3. A method as claimed in claim 1 comprising displaying, in said user interface at said control panel, an input field for an injection formula comprising at least an injection dosage and an injection rate.

4. A method as claimed in claim 1 wherein said control panel is part of a control unit for said magnetic resonance imaging scanner, and comprising, upon connection of said contrast agent injector to said magnetic resonance imaging scanner, automatically recognizing at said control unit an injector type of said contrast agent injector, and displaying, as said user interface at said control panel, a user interface corresponding to said injector type.

5. A method as claimed in claim 1 wherein said control panel is a part of a control unit for said magnetic resonance imaging scanner, and wherein said control unit comprises an input device and comprising entering, via said input device, an injector type of said contrast agent injector and displaying, as said user interface at said control panel, a user interface corresponding to said injector type.

6. A method as claimed in claim 1 wherein said contrast agent injector has a display at which an injector user interface is displayed, and comprising transmitting said injector user interface from said contrast agent injector to said control panel via said communication path, and displaying said injector user interface as said user interface at said control panel.

7. A method as claimed in claim 1 comprising automatically formulating and displaying, at said user interface at said control panel, a recommendation for said final operating parameters for configuring said contrast agent injector, based on the evaluation of said information.

8. A method as claimed in claim 1 wherein said injector has a standby mode in which injection of contrast agent by said contrast agent injector is possible, and a safe mode in which injection of contrast agent by said contrast agent injector is not possible, and comprising displaying a switch at said user interface at said control panel allowing selective switching between said standby mode and said safe mode from said control panel.

9. A method as claimed in claim 8 comprising transmitting a mode status from said contrast agent injector to said magnetic resonance imaging scanner indicating whether said contrast agent injector is currently in said standby mode or said safe mode, and automatically displaying a warning at said user interface at said control panel if an instruction is entered via said user interface to start operation of said magnetic resonance imaging scanner when said contrast agent injector is in said safe mode.

10. A method as claimed in claim 8 comprising automatically displaying a message at said user interface at said control panel when said contrast agent injector is switched to said standby mode.

11. A magnetic resonance imaging apparatus comprising:
    a magnetic resonance scanner;
    a control unit that operates said scanner, said control unit having a displayed control panel;
    a contrast agent injector;
    a communication path between said contrast agent injector, and said control unit of the scanner;
    said control unit being configured to display a user interface for said contrast agent injector at said control panel of said magnetic resonance scanner;
    said control unit being configured to configure and display preliminary operating parameters for said contrast agent injector based on entries made via said user interface displayed at said control panel;
    a memory comprising a database in which information is stored that is relevant to treatment of a specific patient with contrast agent; and
    said control unit being configured to access said information from said database and to display said information at said user interface, and to automatically evaluate, dependent on said information, said preliminary operating parameters for said contrast agent injector and, when evaluation of said operating parameters dependent on said information indicates the preliminary operating parameters are not appropriate for said specific patient, to automatically cause a warning to be displayed at said user interface, and to automatically generate final operating parameters for said contrast agent injector from said preliminary operating parameters, and to control operation of said contrast agent injector according to said final operating parameters.

* * * * *